United States Patent [19]

Smedley et al.

[11] Patent Number: 5,240,146
[45] Date of Patent: Aug. 31, 1993

[54] VARIABLE PROPORTION DISPENSER

[76] Inventors: William H. Smedley, 33285 Blanche Dr., Lake Elsinore, Calif. 92330; Clark B. Foster, 23631 Wakefield Ct., Laguna Niguel, Calif. 92677; Terry M. Haber, 25011 Castlewood, Lake Forest, Calif. 92630

[21] Appl. No.: 808,717

[22] Filed: Dec. 17, 1991

Related U.S. Application Data

[63] Continuation-in-part of Ser. No. 628,271, Dec. 14, 1990, abandoned, which is a continuation-in-part of Ser. No. 781,398, Jun. 21, 1991, which is a continuation-in-part of Ser. No. 667,319, Mar. 8, 1991, Pat. No. 5,147,323, which is a continuation-in-part of Ser. No. 668,278, Mar. 8, 1991.

[51] Int. Cl.⁵ .............................................. A61N 5/00
[52] U.S. Cl. ............................. 222/137; 222/145; 222/309; 222/327; 604/82; 604/186; 604/191
[58] Field of Search ............ 222/137, 145, 283, 309, 222/327, 386; 604/135, 326, 82, 186, 191

[56] References Cited

U.S. PATENT DOCUMENTS

| | | | |
|---|---|---|---|
| 3,162,217 | 12/1964 | Poli, Jr. et al. | 222/309 |
| 3,248,950 | 5/1966 | Pursell et al. | 222/309 |
| 3,283,727 | 11/1966 | Rodrigues, Jr. | 222/309 |
| 3,343,539 | 9/1967 | Moorhouse | 222/309 |
| 3,831,602 | 8/1974 | Broadwin | 222/309 X |
| 4,040,420 | 8/1977 | Speer | 604/182 |
| 4,044,757 | 8/1977 | McWhorter et al. | 128/2 A |
| 4,273,778 | 5/1983 | Kozan et al. | 604/191 |
| 4,610,666 | 9/1986 | Pizzino | 604/191 |
| 4,631,055 | 12/1986 | Redl et al. | 604/82 |
| 4,666,430 | 5/1987 | Brown et al. | 604/141 |
| 4,801,434 | 1/1989 | Kido et al. | 222/135 X |
| 4,846,405 | 7/1989 | Zimmermann | 239/422 |
| 4,874,368 | 10/1989 | Miller et al. | 604/82 |
| 4,883,472 | 11/1989 | Michel | 222/386 X |
| 4,962,868 | 10/1990 | Borchard | 222/386 X |
| 4,978,336 | 12/1990 | Capozzi et al. | 604/82 |
| 5,019,048 | 5/1991 | Margolin | 604/153 |

FOREIGN PATENT DOCUMENTS

| | | | |
|---|---|---|---|
| 313519 | 4/1989 | European Pat. Off. | 222/137 |
| 137660 | 10/1901 | Fed. Rep. of Germany | 604/191 |
| 984352 | 7/1951 | France | 222/309 |
| 1051010 | 1/1954 | France | 604/82 |
| 1054173 | 3/1954 | France | 604/82 |
| 245816 | 5/1987 | German Democratic Rep. | 603/191 |
| 733168 | 7/1955 | United Kingdom | 222/309 |

OTHER PUBLICATIONS

Brochure "How to Use Your *NovolinPen* TM," Sep. 1990, Novo Nordisk A/S.
Brochure "Product Information for the *Novo Pen* ® Insulin Delivery System," issue 1988, Squibb–Novo, Inc.
Brochure "Product Information for the *Novoline-Pen* TM Insulin Delivery System," issued 1988, Squibb–Novo, Inc.

*Primary Examiner*—Andres Kashnikow
*Assistant Examiner*—Anthoula Pomrening
*Attorney, Agent, or Firm*—Townsend and Townsend Khourie and Crew

[57] ABSTRACT

A variable proportion dispenser (2) includes a housing (4) which houses two pharmaceutical cartridges (6, 7). A reciprocating drive assembly (10) includes a drive stem (36, 37) extending from the piston (46) of each cartridge, a sliding body (66) mounted to the housing, and two one-way drive devices (54, 55) carried by the sliding body. Each one-way drive device includes a threaded dosage adjuster (60 61), and a reciprocating, one-way driver (58, 59) which drives the drive stem into the cartridge. The distance the reciprocating driver can move on the return stroke away from the cartridge is adjustable by changing the threaded position of the dosage adjuster within the sliding body to change if and when the opposed ends (98, 96) of the dosage adjuster and reciprocating driver disengage during the return stroke. During the next delivery stroke, the separated opposed ends (98, 96) do not contact for an initial portion of the stroke. The user can thus control the amount and proportion of each pharmaceutical dispensed during each delivery stroke for each dispensing cycle.

16 Claims, 11 Drawing Sheets

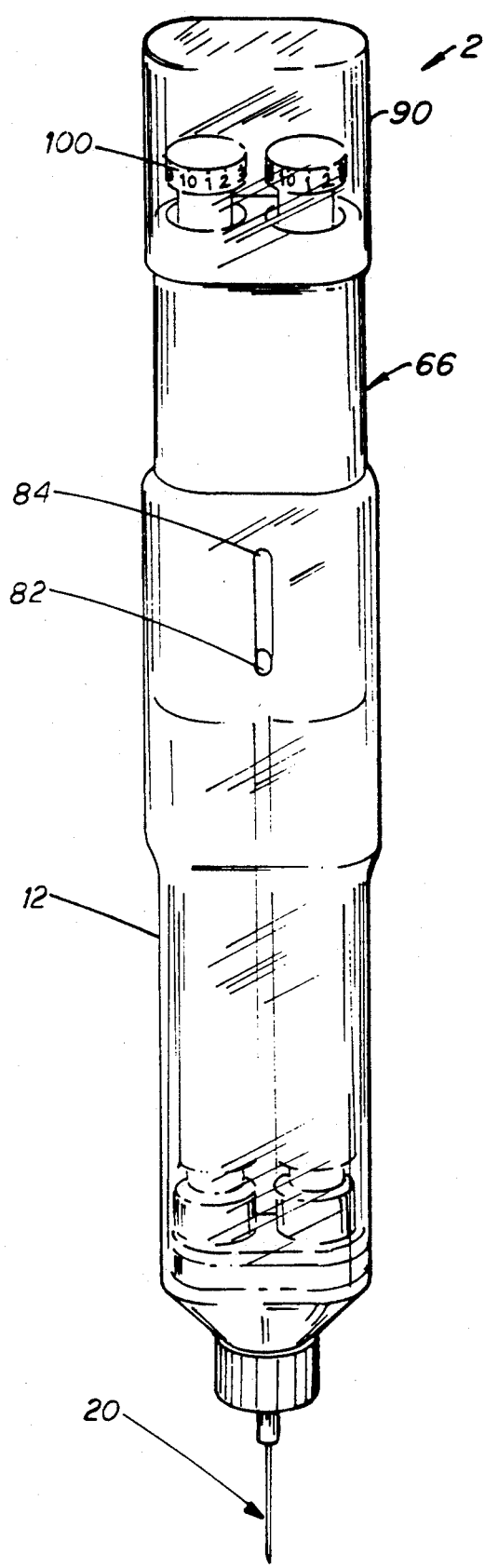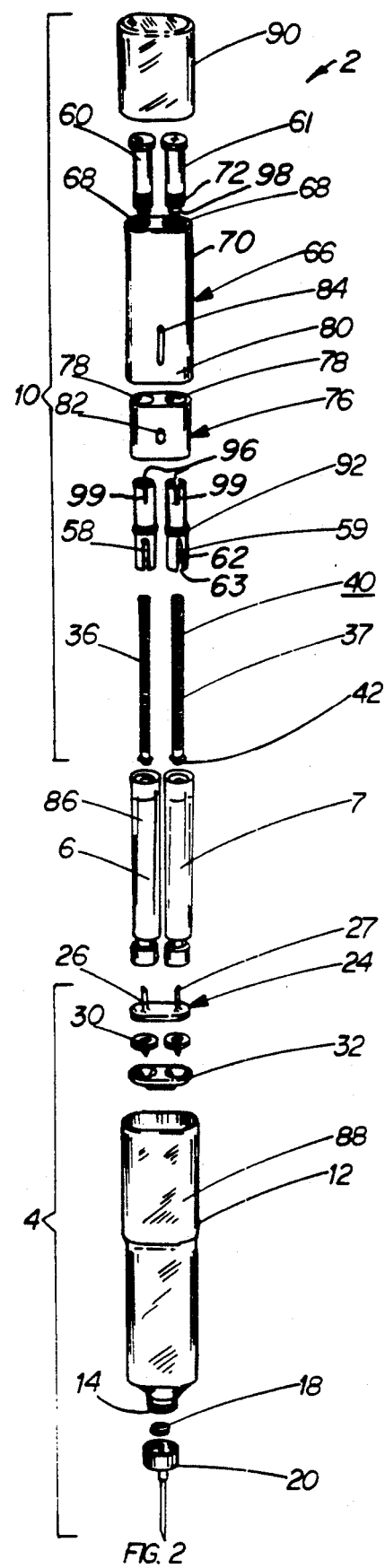
FIG. 1
FIG. 2

VARIABLE PROPORTION DISPENSER

This is a continuation-in-part of U.S. patent application Ser. No. 07/628,271 filed Dec. 14, 1990 entitled Variable Proportion Dispenser, now abandoned, and a continuation-in-part of U.S. patent application Ser. No. 07/718,398 filed Jun. 21, 1991, entitled Multiple Pharmaceutical Syringe, which is a continuation-in-part of both U.S. patent application Ser. No. 07/668,278, filed Mar. 8, 1991 and entitled Multipharmaceutical Syringe, and of U.S. patent application Ser. No. 167,319, filed Mar. 1991 and now U.S. Pat. No. 5,147,323 issued Sep. 15,1992 and entitled Multiple Cartridge Syringe, the disclosures of which are incorporated by reference.

BACKGROUND OF THE INVENTION

Human insulin is of two basic types: regular and NPH. Insulin users use all regular insulin, all NPH or a mixture of the two insulins, typically 70% NPH and 30% regular. However, if one were to want a combination of regular and NPH other than the commercially available 70%/30% mixture, the user would need to have two sets of insulin injection syringes and would have to make two separate injections.

SUMMARY OF THE INVENTION

The present invention is directed to a variable proportion dispenser, especially useful for dispensing different types of insulin in amounts and proportions selected by the user. Once the combined dosage is selected, both in amount and proportion, the same dosage will be automatically provided for each actuation cycle of the dispenser. The invention, as an insulin delivery system, permits the total amount of the insulin injected and the proportion NPH and regular human insulin to be user selected.

The variable proportion dispenser includes a housing which houses two or more variable volume containers, typically pharmaceutical cartridges. A reciprocating drive assembly is used to dispense predetermined amounts of the contents of the cartridges in predetermined proportions. The amounts and proportions, once set, remain the same for each actuation of the drive assembly. The reciprocating drive assembly includes a sliding body mounted to the housing. The sliding body moves between first and second axial positions during each cycle of the dispenser.

The drive assembly also includes a one-way drive device carried by the sliding body and a drive stem engaged by the one-way drive device during each delivery stroke. The one-way drive device preferably includes a threaded dosage adjuster which mounts within a threaded hole within the sliding body. The one-way drive device also includes a reciprocating driver positioned between dosage adjuster and the cartridge. The dosage adjuster and reciprocating driver are axially aligned and configured so that when the sliding body, and dosage adjuster therewith, are driven during the delivery stroke from the first position towards the second position, that is towards the cartridge, the opposed ends of the dosage adjuster and reciprocating driver engage and the reciprocating driver is driven towards the cartridge. The reciprocating driver has a lower end which engages the drive stem during the delivery stroke to drive the drive stem against the piston in the cartridge. The lower end of the reciprocating driver and the drive stem are configured so the reciprocating drive ratchets back over the drive stem during the return stroke. Thus, the reciprocating driver acts as a one-way linear driver.

The reciprocating driver preferably has a collar positioned to engage a driver stop associated with the housing to limit the movement of the reciprocating driver on the return stroke away from the cartridge. Whether or not the collar contacts the driver stop is determined by the axial position of the dosage adjuster within the sliding body. For example, if the dosage adjuster is fully threaded into the sliding body, the collar will typically not contact the driver stop so that the adjacent ends of the dosage adjuster and reciprocating driver remain engaged throughout the cycle. However, if the dosage adjuster is moved away from the fully threaded position a sufficient amount, then the collar will contact the driver stop before the sliding body has reached its first position on the return stroke. This causes the opposed ends of the dosage adjuster and reciprocating driver to disengage. During the next delivery stroke, during which the sliding body is moved from the first position to the second position, the dosage adjuster does not contact the reciprocating driver for an initial portion of the stroke. This results in a decrease in the volume of the contents driven from the cartridge. Also, by individually adjusting the dosage adjusters, the point at which the dosage adjusters contact their respective reciprocating drivers can be changed. This permits the user to adjust the proportions and amounts of the components dispensed from the cartridges during each delivery stroke.

Another aspect of the invention is the provision of a visual indicator which permits the user to easily determine the amount of each component which is to be delivered before the delivery stroke. In one embodiment this is achieved using a visual dose indicator which moves axially according to the proposed dose. A separate dose indicator is used for each component.

Some users may suffer from a certain degree of confusion; the simultaneous visual display of two (or more) dose indicators when setting the dose for each component could create problems for these users. With a two-component dispenser, it is preferred that the dose indicator for each component be visually perceptible from opposite sides of the dispenser. Thus, when a user sets the dose, by rotating the dose adjustor, only one dose indicator is visible. This helps to ensure that the user does not become confused as to the dose selected.

In the present embodiments the axial position of the reciprocating driver prior to the delivery stroke determines the dose. The visual indication of this axial movement can be magnified by the dose indicator. For example, assume that an axial movement of three millimeters by the reciprocating driver corresponds to one unit of medication. With the present invention, the dose indicator can be driven in such a way that the dose indicator moves six millimeters for every three millimeters the reciprocating driver moves. This permits the units of medication markings, typically carried by the sliding body, to be spaced twice as far apart as would otherwise be possible thus greatly enhancing ease of use and accuracy. Of course, other ratios between the movement of the dose indicator and the movement of the reciprocating driver, and thus of the piston within the cartridge (either greater than one-to-one or less than one-to-one) could be used as well.

In one embodiment the amplification is achieved by providing two sets of threads on the threaded dose adjustor. For example, a right-hand set of threads can be used to drive the dose adjustor within the sliding body and a left-hand set of threads, also on the dose adjustor, can be used to drive the dose indicator. The right-hand threads on the dose adjustor, which engage right-hand threads within the sliding body, cause the dose adjustor to move one pitch length for each rotation of the dose adjustor. However, the dose indicator engages the left-hand threads of the dose adjustor and is prevented from rotating with the dose adjustor but is allowed to move axially. This causes the dose indicator to move one pitch length along the dose adjustor. Thus, the dose indicator moves within the sliding body two pitch lengths for each pitch length the dose adjustor moves. Accordingly, assuming the thread pitches of the left and right-hand threads are the same, the dose indicator moves twice the distance the dose adjustor moves within the sliding body. After the delivery stroke, once the user returns the sliding body back to its predelivery stroke, the dose adjustor and the dose indicator will return to the same positions within the sliding body as before the delivery stroke. Thus, if the user wishes to repeat a stroke with the same proportions, no adjustments need to be made.

One of the primary advantages of the invention is that it permits the user to adjust both the quantity and proportion of the two components to be delivered by the dispenser. The setting stays the same for multiple doses without the need for any additional adjustment.

Other features and advantages of the invention will appear from the following description in which the preferred embodiments have been set forth in detail in conjunction with the accompanying drawings.

BRIEF DESCRIPTION OF THE DRAWINGS

FIG. 1 is an overall isometric view of a variable proportion dispenser made according to the invention with the sliding body in the first, pre-delivery position;

FIG. 2 is an exploded isometric view of the dispenser of FIG. 1;

DESCRIPTION OF THE PREFERRED EMBODIMENT

FIG. 1 illustrates a variable proportion dispenser 2 particularly suited for dispensing insulin. As shown in FIG. 2, dispenser 2 includes broadly a housing assembly 4, first and second insulin containing cartridges 6, 7 and a reciprocating drive assembly 10.

Figure 3:
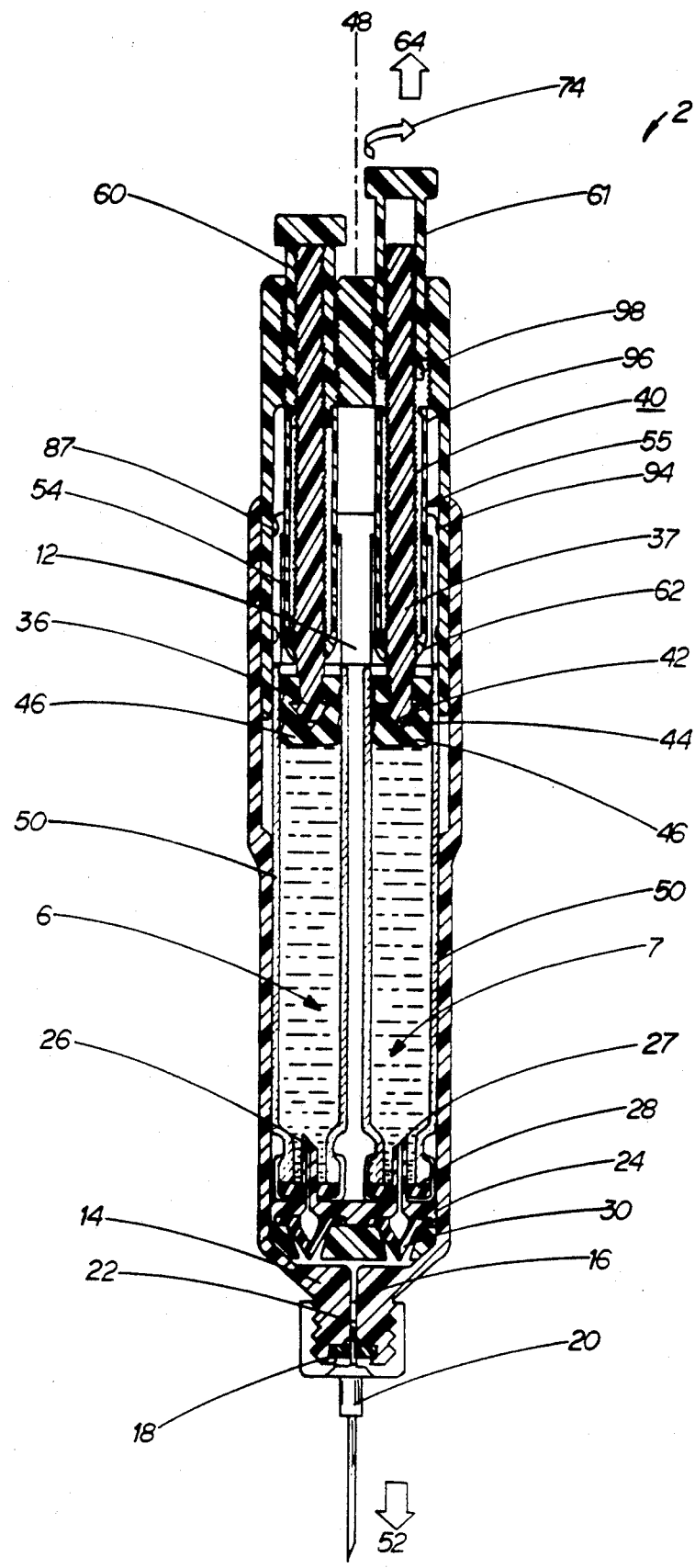
FIG. 3 is a cross sectional view of the dispenser of FIG. 1 with the cap removed, the sliding body in the first, predelivery position and one of the dosage adjusters repositioned within the sliding body.

Turning now also to FIG. 3, housing assembly 4 is seen to include a housing 12, preferably made of a clear plastic material such as polycarbonate, so the user can see the contents of cartridges 6, 7. Housing 12 includes a threaded tip 14 having a central bore 16 formed therein. An elastomeric septum 18 is mounted to the end of tip 14. A double-ended needle assembly 20 has an inner end 22 which pierces septum 18 and is positioned within bore 16 to provide a conduit from bore 16 through needle assembly 20 during use. Needle assembly 20 is preferably replaced after each use.

Cartridges 6, 7 are housed within the interior of housing 12. A dual spike 24 having sharpened spike tips 26, 27 is used to pierce the septums 28 at the ends of cartridges 6, 7. A pair of elastomeric check valves 30 are positioned adjacent dual spike 24 by a check valve adapter 32. As shown in FIG. 3, this provides a pathway from the interiors of cartridges 6, 7, through spike tips 26, 27, past check valves 30, into bore 16 and through needle assembly 20. However, the capillary restrictions created within spike tips 26, 27 and needle assembly 20 and the restrictions provided by check valves 30 and septum 18 keep the contents of cartridges 6, 7 from leaking from dispenser 2.

Reciprocating drive assembly 10 includes first and second drive stems 36, 37 having serrated outer surfaces 40 and coned tips 42. Coned tips 42 are housed within complementary regions 44 formed within pistons 46 of cartridges 6, 7. Thus, movement of drive stems 36, 37 parallel to axis 48 will drive pistons 46 within the barrels 50 of cartridges 6, 7. Drive stems 36, 37 are driven in the direction of arrow 52 by one-way drive devices 54, 55. Drive devices 54, 55 include reciprocating drivers 58, 59 and dosage adjusters 60, 61. Devices 54, 55 are hollow to accommodate drive stems 36, 37. Drivers 58, 59 each include a stem engaging end 62 having serrations or teeth which complementarily engage the serrated outer surface 40 of its associated drive stem 36, 37. The serrations or teeth are configured such that movement of reciprocating drivers 58, 59 in the direction of arrow 52 causes stem engaging ends 62 to firmly grip the associated drive stems 36, 37, thus forcing piston 46 in the direction of arrow 52. However, movement in the direction of arrow 64, that is in the direction of the return stroke, allows stem engaging end 62, which has slits 63 which allow end 62 to dilate, to slide over serrated outer surface 40 so that the reciprocal movement of reciprocating drivers 58, 59 act in a ratcheting manner driving pistons 46 in the direction of arrow 52 but not in the reverse direction of arrow 64.

Reciprocating drive assembly 10 also includes a sliding body 66 having a pair of internally threaded holes 68 formed at one end 70 of sliding body 66. Dosage adjusters 60, 61 each include external threads 72 which engage threaded holes 68 to permit the user to adjust the axial positions of dosage adjusters 60, 61 relative to sliding body 66 as suggested in FIG. 3 by arrow 74.

Reciprocating drive assembly 10 also includes a limit guide 76 having parallel bores 78 through which reciprocating drivers 58, 59 and drive stems 36, 37 pass. The lower end 80 of sliding body 66 is hollow for receipt of limit guide 76. Limit guide 76 has an outwardly projecting rib 82, see FIGS. 1 and 2, which rides within an axially extending slot 84 formed in end 80 of sliding body 66. Limit guide 76 is secured to housing 12 through the attachment of rib 82 to the inner wall of housing 12. The upper portion 88 of housing 12 is enlarged to accommodate sliding body 66. Movement of sliding body 66 and dosage adjusters 60, 61 is limited by engagement of rib 82 with the ends of slot 84. Sliding body 66 includes projections 87 which engage appropriately positioned indentations 89, 91 formed in limit guide 76 to act as detentes to help keep sliding body 66 in the pre-delivery and post-delivery positions.

Figure 3A:
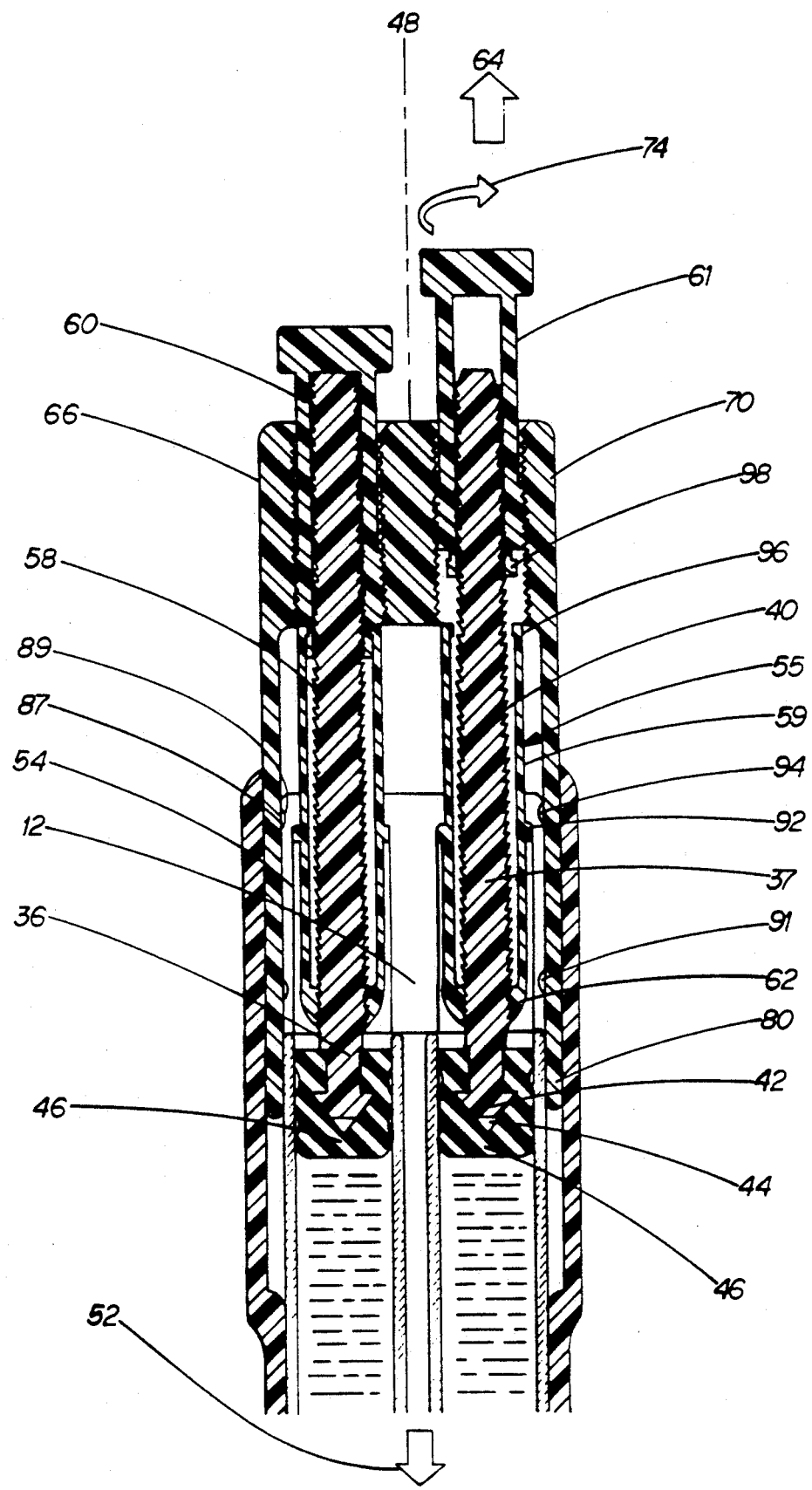
FIG. 3A is an enlarged view of a portion of the dispenser of FIG. 3.

Dispenser 2 is shown in FIG. 3 after a cap 90 has been removed, after sliding body has been moved from its second, post-delivery position of FIG. 1 to its first, predelivery position, and after dosage adjuster 61 has been adjusted by rotating in the direction of arrow 74. Doing so causes dosage adjuster 61 to separate from reciprocating driver 59 as shown in FIG. 3. This occurs because reciprocating driver has a collar 92 which engages an inwardly extending, annular driver stop 94 to prevent any further movement of reciprocating driver 59 in the direction of arrow 64. As seen in FIG. 3A, the ends 96, 98 of reciprocating driver 59 and the dosage adjuster 61 are configured to provide non-slip driving engagement when dosage adjuster 61 is moved in the direction of arrow 52 but for releasable engagement when dosage adjuster 61 is moved in the direction of arrow 64 once a sufficient separating force is applied between the reciprocating driver 59 and dosage adjuster 61.

Figure 4:
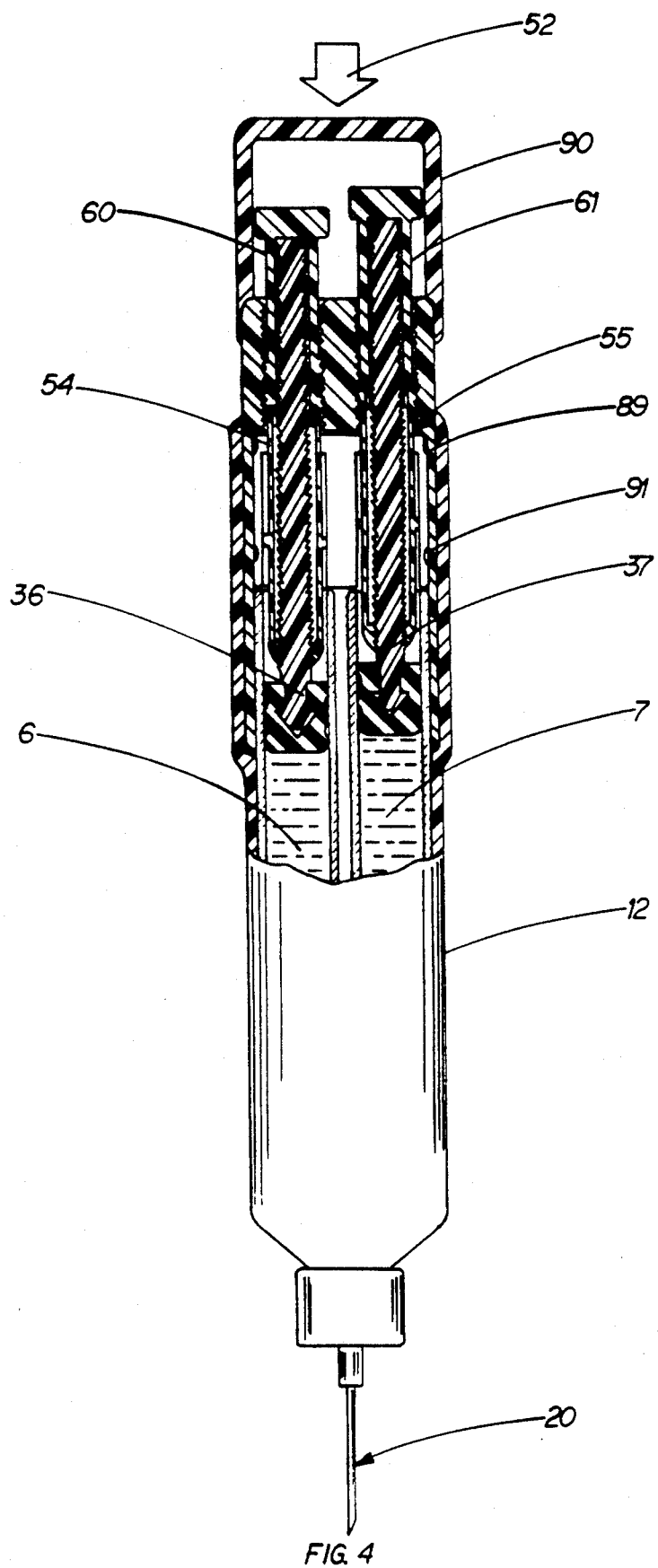
FIG. 4 shows the dispenser of FIG. 3 with the cap replaced and with the sliding body in the second, post-delivery position following dispensing of the two components in different proportions.
Figure 4A:
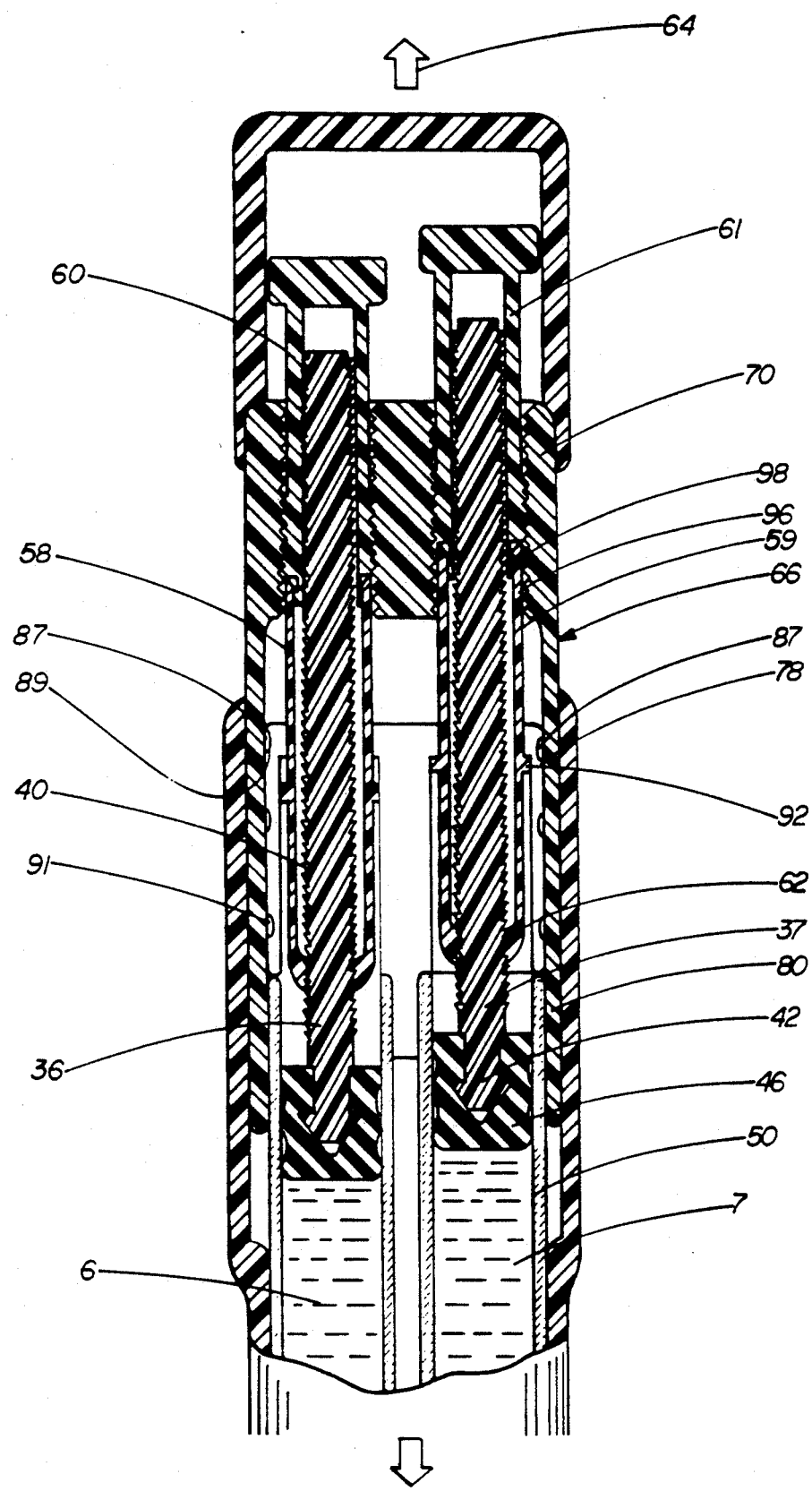

FIG. 4 shows dispenser 2 with cap 90 replaced and after reciprocating drive assembly 10 has been moved in the direction of arrow 52 during a delivery stroke from the pre-delivery condition of FIG. 3 to post-delivery condition of FIG. 4. Although not shown, rib 82 is in the position shown in FIG. 1 at the lower end of slot 84, rib 82 and slot 84 defining the limits of movement of drive assembly 10. Also, by comparing the positions of pistons 46 of cartridges 6, 7 it can be seen that a greater amount of the contents of cartridge 6 has been expulsed than of cartridge 7. This is due to the extra distance dosage adjuster 61 must travel before ends 96, 98 of reciprocating driver 59 and dosage adjuster 61 meet as compared with the corresponding ends of driver 58 and adjuster 60. The use of check valves 30 keep the contents of one cartridge 6, 7 from moving into the interior of the other cartridge 7, 6.

Figure 5:
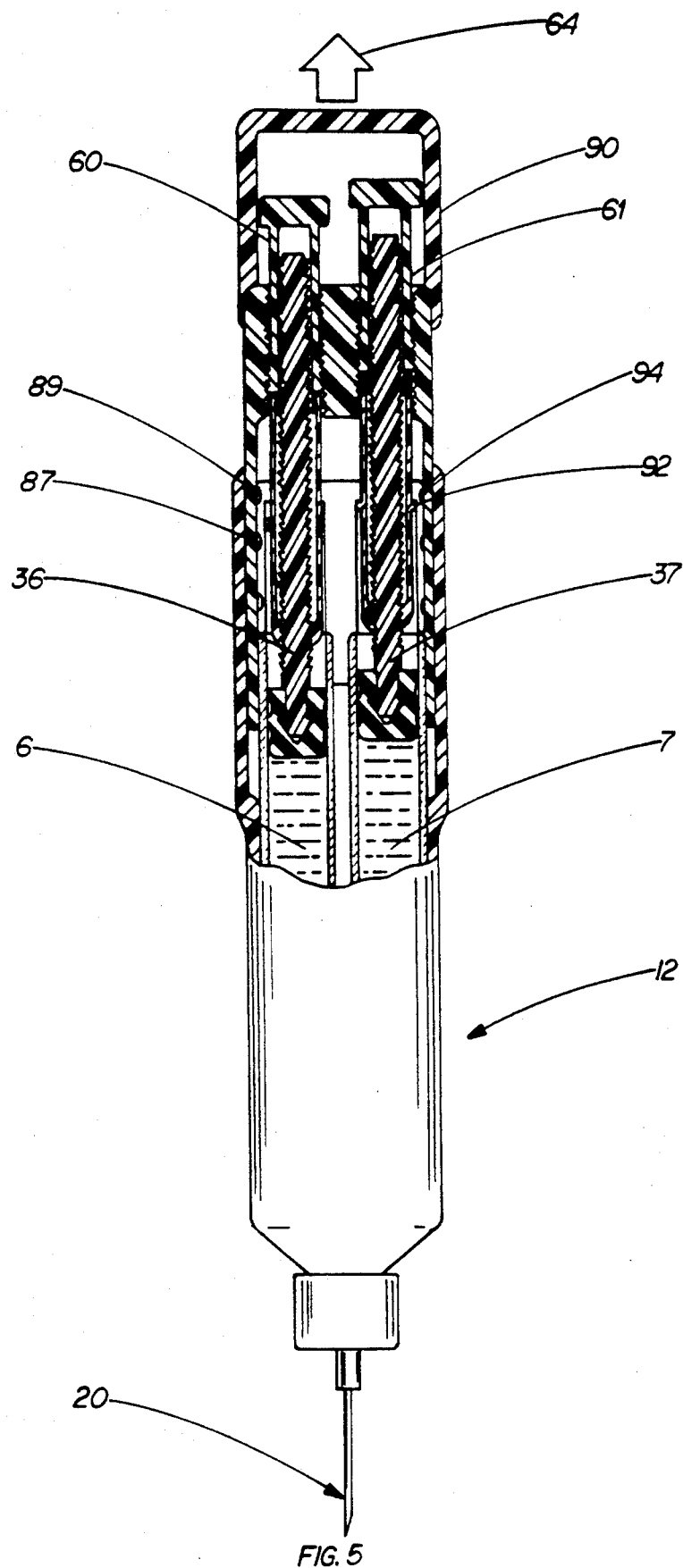
FIG. 5 shows the dispenser of FIG. 4 with the sliding body moved from the post-delivery position of FIG. 4 to an intermediate position.

FIG. 5 illustrates variable proportion dispenser 2 with the reciprocating driver assembly 10 moved to an intermediate position between the post-delivery position of FIG. 4 by pulling in the direction of arrow 64. At this point, rib 82, not shown in FIG. 5, is mid-way along slot 84 but collar 92 of reciprocating driver 59 has engaged driver stop 94 while collar 92 of reciprocating 58 has not. Further movement of drive assembly 10 in the direction of arrow 64 will cause ends 96, 98 of one-way drive device 55 to separate as in FIG. 3. The engagement and separation of ends 96, 98 is facilitated by slits 99 in drivers 58, 59 which permit ends 96 to dilate.

To use dispenser 2, a new needle assembly 20 is generally mounted to tip 14 of housing 12. Cap 90 is removed is removed and dosage adjusters 60, 61 are each rotated according to the amount and proportions of the contents of cartridges 6, 7 to be injected per cycle. That is, for maximum dosage, the dosage adjusters 60, 61 are kept fully engaged within threaded holes 68 to minimize the distance between ends 96, 98. Numerical indicia 100, as suggested in FIG. 1, can be used on dosage adjusters 60, 61 to permit the appropriate injection volume and proportions to be chosen. Cap 90 is then replaced onto end 70 of sliding body 66, sliding body 66 is then moved in the direction of arrow 64 so that rib 82 moves from the position of FIG. 1 at the lower end of slot 84 to the upper end of slot 84. Doing so causes stem engaging ends 62 of reciprocating drivers 58, 59 to slide over drive stems 36, 37 so that pistons 46 do not move during this return stroke. (Friction between pistons 46 and cartridges 6, 7 is sufficient to keep drive stems 36, 37 in place during the return stroke.) Sliding body 66 is then driven downwardly in a delivery stroke in the direction of arrow 52 by pressing on cap 90. The contents of cartridges 6, 7 begin to be expulsed through associated spike tips 26, 27, check valves 30, bore 16 and needle assembly 20. In the configuration of FIG. 3, a greater proportion of the contents of cartridge 6 is expulsed through needle assembly 20 than of cartridge 7 because of the relative positions of dosage adjusters 60, 61. After use, needle assembly 20 can be capped or removed and a protective cap, not shown, can be mounted to tip 14 until the next use. To give another injection with the same volume and in the same proportions, one merely replaces needle assembly 20, if required, and moves sliding body 66 in a return stroke in the direction of arrow 64 and then in a delivery stroke in the direction of arrow 52, thus repeating the process.

The present invention has been described with reference to two cartridges 6, 7. The invention may be practiced with three or more cartridges as well. Also, other types of variable volume containers instead of pharmaceutical cartridges could also be used. For example, a collapsible bellows arrangement or a collapsible bag or sack could be used instead of the cartridges. Although the outer surfaces 40 of driver stems 36, 37 are serrated or toothed to provide a good ratcheting surface, the outer surfaces could be smooth as well by using other types of one-way drivers. The present invention is shown in an embodiment in which either component can be varied over a large range, preferably a range of 0% to 100%. If desired, adjustment devices could be provided that do not give such a wide range. For example, the adjustments could be such that the percentages of the components only range from 20% to 80% rather than 0% to 100%. In the preferred embodiment both the total volume of the dosage and the proportions are adjusted using dosage adjusters 60, 61. The total volume dispensed could also be adjusted by adjusting the effective length of slot 84. In addition, one of the components could be non-adjustable so that all adjustment in proportion would be through the reciprocating drive assembly for the other component; this might be useful when a separate means for adjusting the total volume dispensed is used, such as adjusting the effective length of slot 84. Dosage adjusters 60, 61 could also be coupled to one another through different sized gears. For example, dosage adjuster 60 could have 10-tooth gear while dosage adjuster 61 could have a 6-tooth gear so that every revolution of dosage adjuster 60 would cause dosage adjuster 61 to rotate one and two-third times. This could be useful if the ratio of the components is known and only the total volume is to be changed. Of course, different sets of gears for different ratios could be provided.

FIGS. 6–8B illustrate an alternative embodiment of the invention shown in FIGS. 1–5. Dispenser 2a is similar to dispenser 2 with corresponding reference numerals referring to corresponding parts; therefore parts which are identical will not be described separately. The primary differences between dispensers 2, 2a relate to the construction of dose adjustors 60a, 61a, sliding body 66a and check valve 30a.

Figure 7:
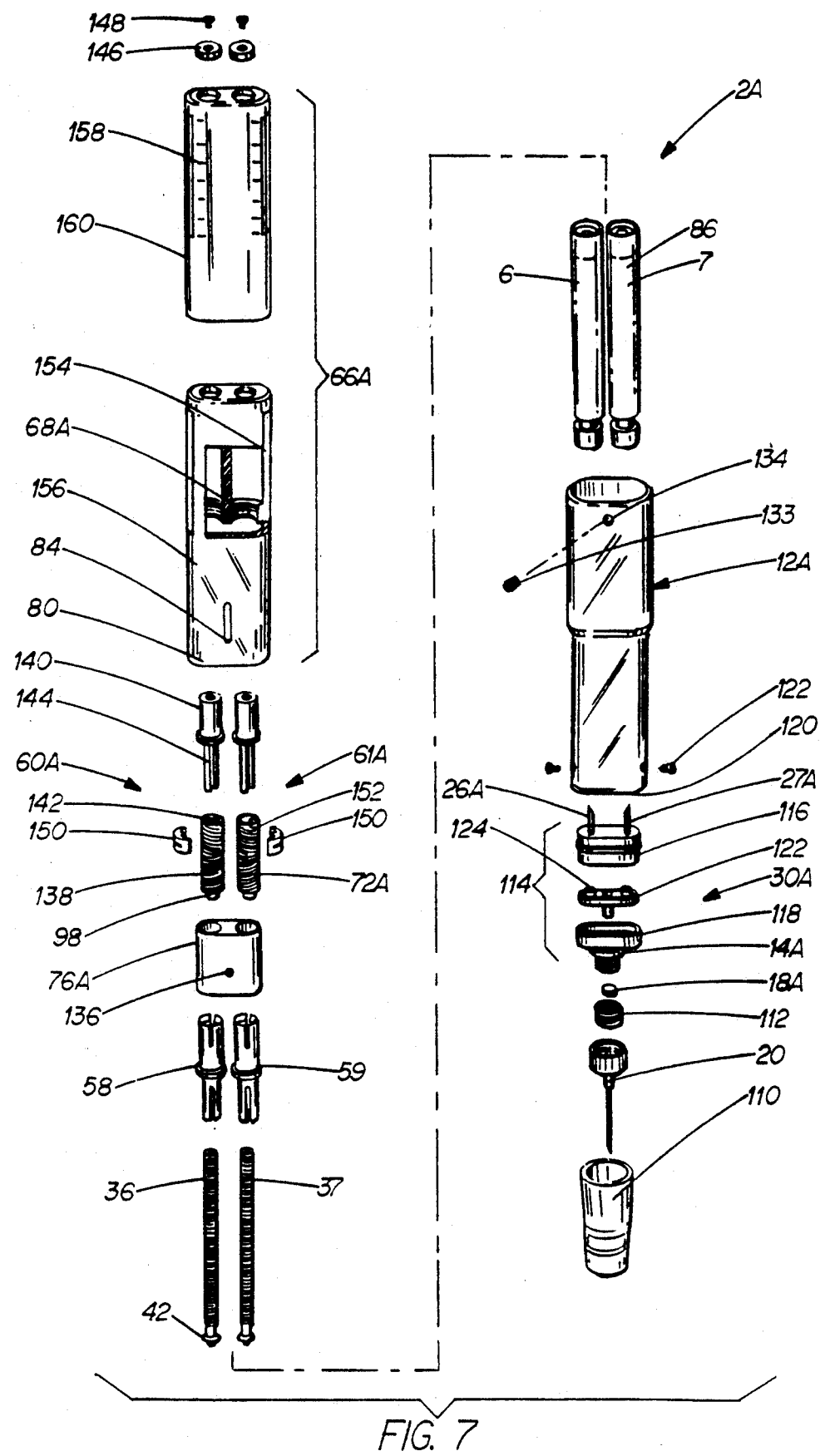
FIG. 7 is an exploded isometric view of the dispenser of FIG. 6.
Figure 8:
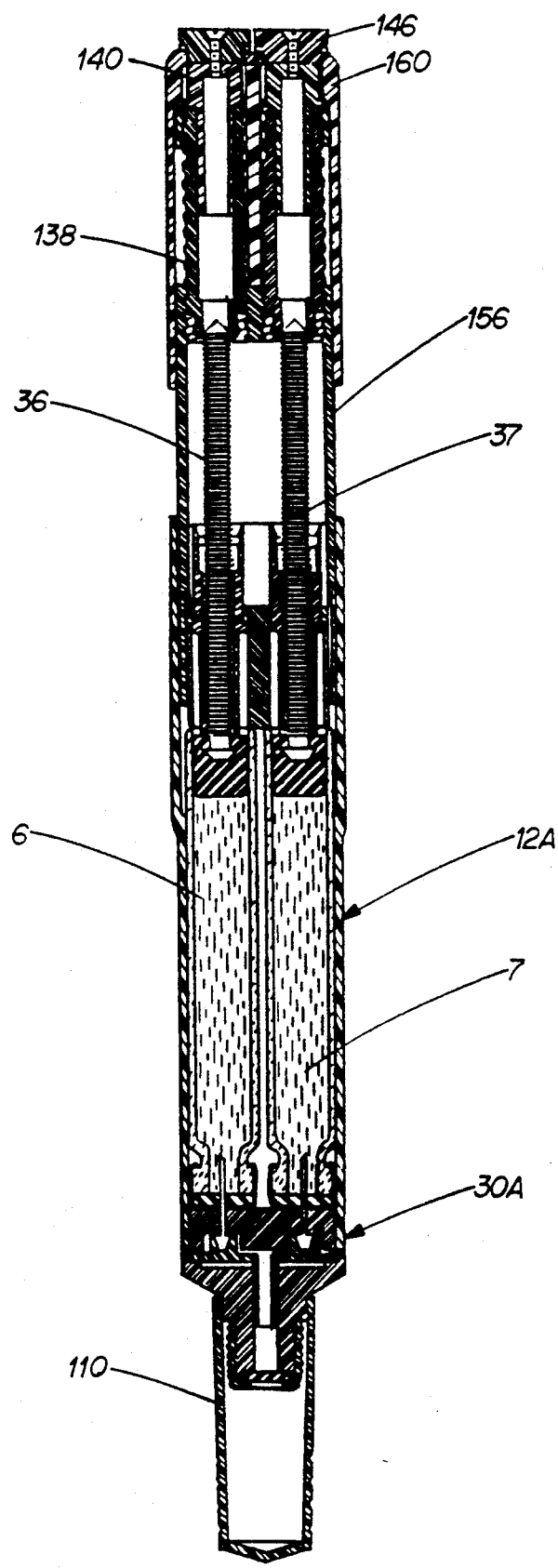
FIG. 8 is a cross-sectional view of the dispenser of FIG. 6 in the first, predelivery position.
Figure 8A:
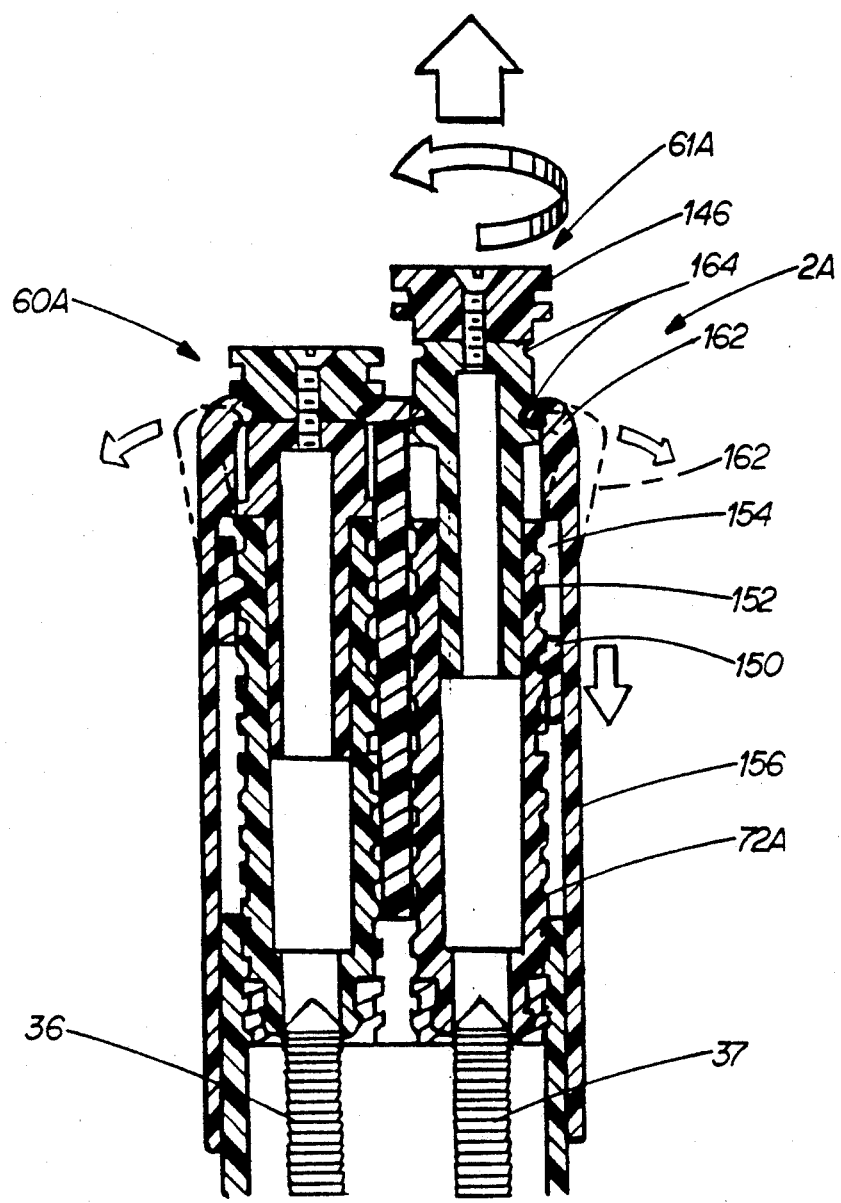
FIG. 8A is an enlarged cross-sectional view of a portion of the dispenser of FIG. 8 with the right-hand dose adjustor axially pulled away from the sliding body and after having been rotated two complete revolutions so the dose indicator has moved within the sliding body a distance equal to four pitch lengths.
Figure 8B:
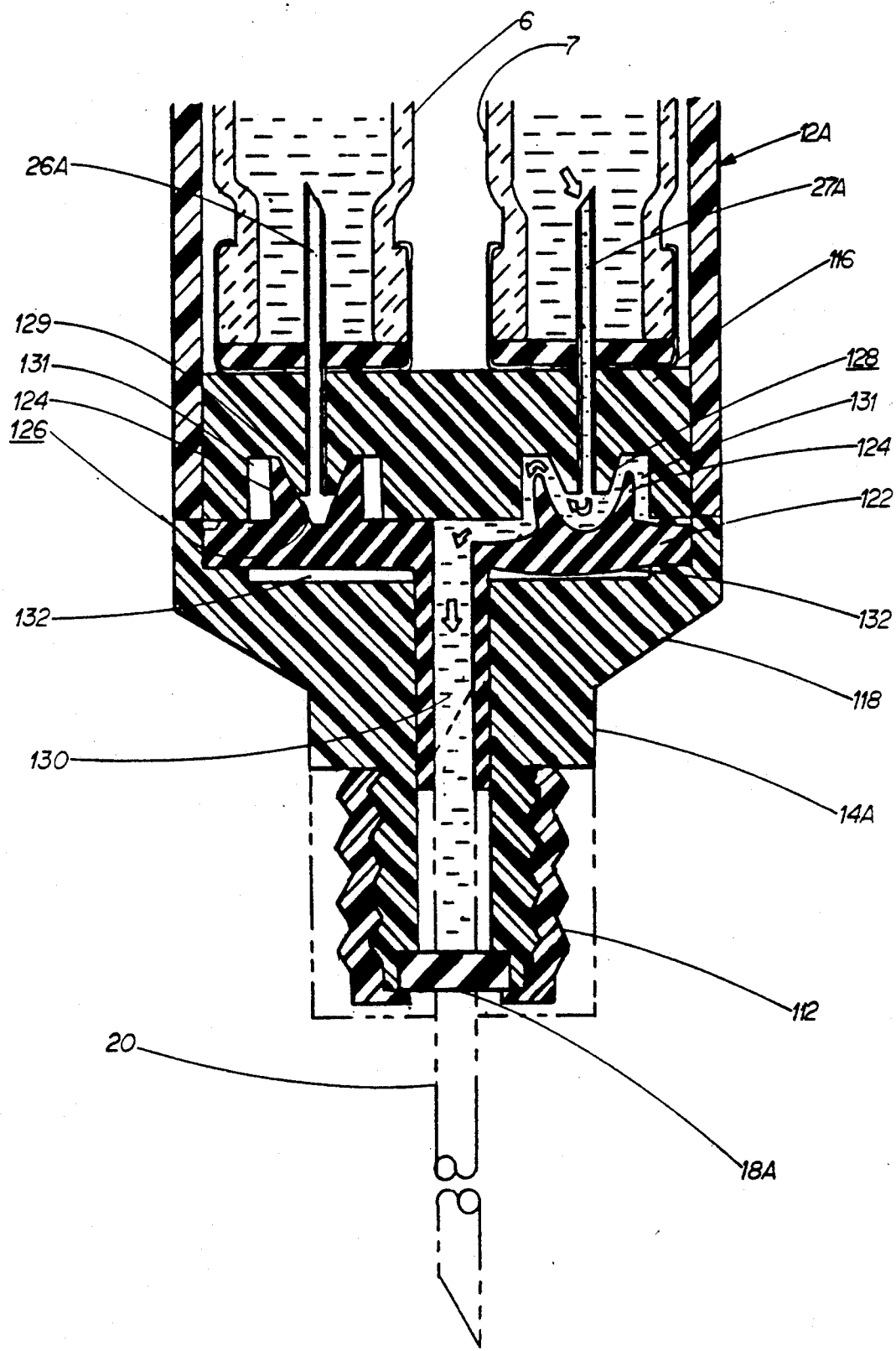
FIG. 8B is an enlarged cross-sectional view of the lower portion of the dispenser of FIG. 8 illustrating, in somewhat exaggerated form, fluid flow from the right-hand cartridge, through the spike, past the check valve, through the common passageway and into the double-ended needle shown in phantom.

Referring the reader primarily to FIG. 7, a needle sheath 110 is used to cover needle assembly 20 prior to use for safety. Septum 18a, see FIGS. 8 and 8B, is kept in place on tip 14a by a threaded keeper 112. Check valves 30a are formed differently from check valves 30. A combined check valve and spike assembly 114 includes a spike adapter 116, a manifold 118 and a check valve body 122. Manifold 118 carries tip 14a and is secured to an end 120 of housing 12a, such as through the use of an adhesive. Spike adaptor 116 is mounted within the interior of housing 12a at end 120 of housing 12a and is secured thereto by the use of screws 123 as shown in FIG. 7. Check valve body 122, made from butyl rubber, is positioned between spike adaptor 116 and manifold 118, both made of a hard plastic, such as polycarbonate. Check valve body 122 includes a pair of cup-shaped members 124 each having an internal conical surface 126 positioned to engage an external conical surface 128 formed by the outside of each of two projections 129. Projections 129 are hollow, as shown in FIG. 8A, and are positioned for fluid communication with the interior of hollow spikes 26a, 27a. Together check valve body 122, spike adaptor 116 and manifold 118 combine to create check valves 30a.

Normally, as shown in the left-hand side of FIG. 8B, check valves 30a are closed preventing fluid flow from a common pathway 130, which fluidly connects to the interior of needle cannula 20, to the interior of cartridges 6, 7. However, upon pressurization of the interior of one of the cartridges, such as cartridge 7 in FIG. 8B, the corresponding check valve 30a is opened as illustrated by the deformation of check valve body 122 and the arrows indicating fluid flow in FIG. 8B. To permit this deformation, assembly 114 provides an annular gap 131 surrounding cup-shaped members 124 and a further gap 132 in the space between that portion of check valve body 122 adjacent cup-shaped members 124 and manifold 118. The deformation of check valve body 122 into both of these regions is graphically illustrated in FIG. 8B.

The configuration of assembly 114 provides a relatively short, low-volume flow path between cartridges 6, 7 and needle assembly 20. This reduces the amount of residual insulin, or other medication, left along the flow path between injections to reduce the possibility for infection.

In the embodiment of FIG. 2, limit guide 76 is secured within the interior of housing 12 by adhering rib 82, which passes through slot 84, to the interior of the housing. In contrast, dispenser 2a secures limit guide 76a to the interior of housing 12a using a Bet screw 133 which passes through a through hole 134 formed in housing 12a and engages a threaded hole 136 formed in limit guide 76a. Other means for securing limit guide 76a to housing 12a could be used as well.

Dose adjustors 60a, 61a are two-part members having a threaded portion 138 and a telescoping drive extension 140. Threaded portions 138 include two sets of threads. Threads 72a are right-hand threads and engage internally threaded holes 68a in sliding body 66a for the same reasons and in the same manner as external threads 72 engage threaded holes 68 in the embodiment of FIG. 2. Threaded portion 138 has an oblong bore 142 sized to accept a similarly shaped oblong extension 144 of extension 140. The interface between bore 142 and extension 144 permits the free telescoping movement of extension 144 within bore 142 but causes rotary motion applied to extension 140 to rotate threaded portion 138.

Figure 6:
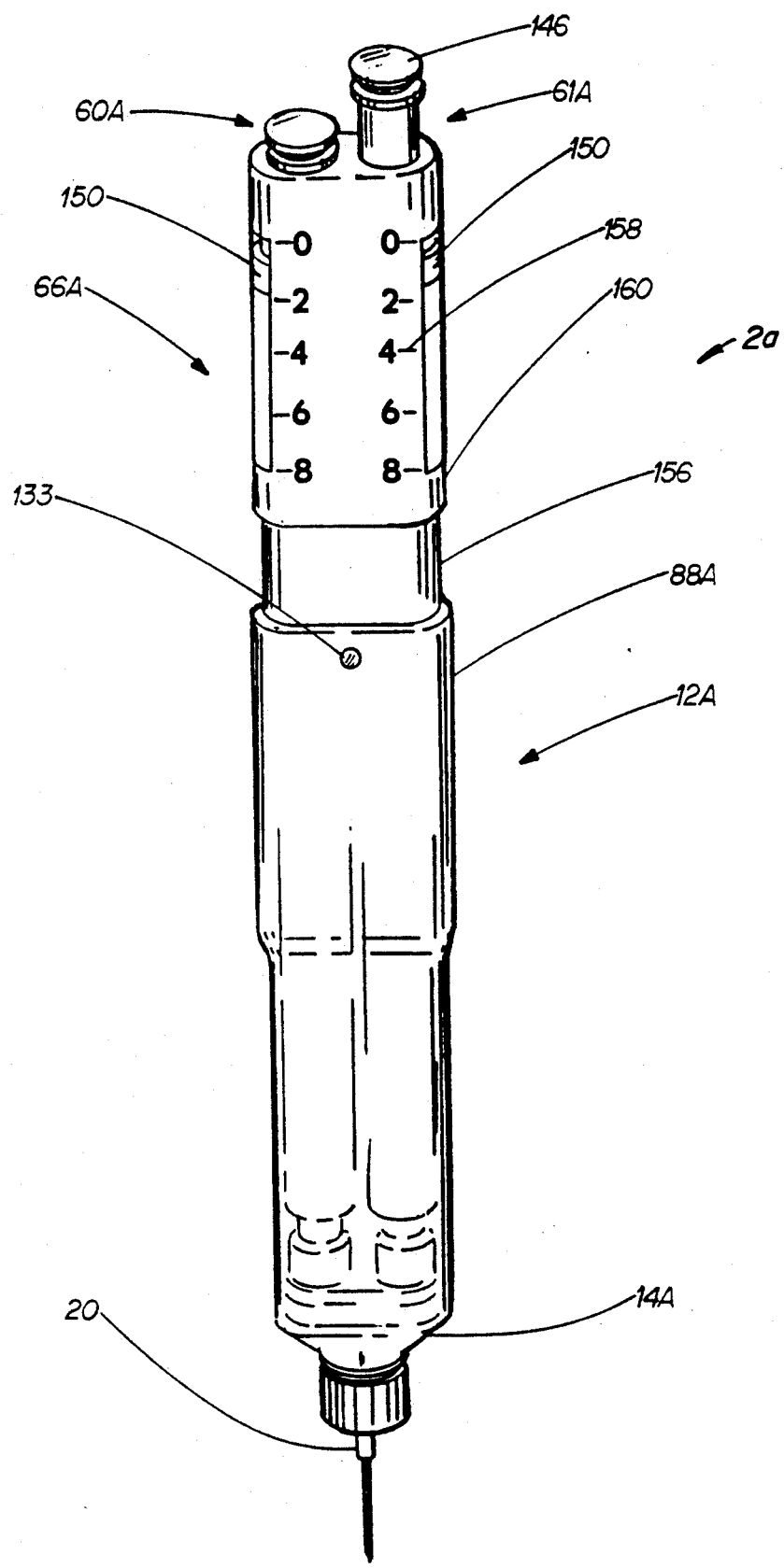
FIG. 6 is an overall isometric view of an alternative embodiment of the variable proportion dispenser shown in FIG. 1 in the first, pre-delivery position with a dosing control knob pulled out away from the sliding body to facilitate adjustment.

As shown in FIG. 6, dose adjustor 60a also includes a dose control knob 146 which is secured to the end of extension 140 by a screw 148. Knob 146 can be grasped by a user and pulled away from sliding body 66a. Doing so permits the user to easily and independently rotate either dose adjustor 60a, 61a as desired without inadvertently rotating the other dose adjustor. For example, in FIGS. 6 and 8A, dose knob 146 of dose adjustor 61a has been pulled away from sliding body 66a to permit the free rotation of the dose adjustor.

Rotation of dose knob 146, in addition to moving threaded portion 138 within sliding body 66a through the engagement of threads 72a and 68a, also causes the movement of a dose indicator 150. Dose indicator 150 engages left-hand threads 152 formed at the end of threaded portion 138 opposite right-hand threads 72a. Dose indicator 150 rides within a cutout 154 formed in the inner part 156 of sliding body 66a. Sliding body 66a also includes a transparent outer part 160, which carries indicator markings 158, mounted over and secured to inner part 156, such as with an adhesive. Cutout 154 keeps dose indicator 150 from moving in a rotary direction while allowing dose indicator 150 to be moved axially. In the preferred embodiment the pitch for threads 72a and 152 is the same. Accordingly, rotating dose knob 146 one complete revolution causes threaded portion 138 to move axially within sliding body 66a one pitch length of threads 72a. However, dose indicator 150, which engages left-hand threads 152 also moves one pitch length along threads 152. Thus, rotating dose knob 146 in a clockwise direction as indicated in FIG. 8A drives threaded portion 138 downwardly in the figure thus carrying dose indicator 150 with it. In addition to this movement, dose indicator 150 is moved one pitch length due to its engagement of the left-hand threads 152. This causes dose indicator 150 to move twice the distance traveled by threaded portion 138 and thus twice the distance travelled by drive stem 37. This magnifies the distance between indicator markings 158 by a two to one margin.

FIG. 8A illustrates dispenser 2a after dose knob 146 of dose adjustor 61a has been pulled outwardly to its operating position. Outer part 160 has a pair of spring fingers 162 formed at its upper end which engage grooves 164 formed in extensions 140. Spring fingers 162 and grooves 164 create detents which provide a positive indication to the user when dose adjustors 60a, 61a are in the retracted or extended positions. It should be noted that the axial movement of dose knob 146 together with extension 140 does not affect the operation of the unit; it only permits the appropriate dose adjustor to be rotated without affecting the rotary position, and thus the dose associated with the rotary position, of the other dose adjustor. If desired, the detents could be made so that the Outermost groove 164 includes a series of notches while the innermost groove 164 is smooth so that, with reference to FIG. 8A, rotary motion of dose adjustor 61a is relatively unrestricted while rotary motion of dose adjustor 60a is substantially hindered or prevented.

Further modifications and variations can be made to the disclosed embodiments without departing from the subject of the invention as defined in the following claims.

What is claimed is:

1. A variable proportion dispenser comprising:
   a housing;
   first and second variable volume containers mounted to the housing and including first and second exits and first and second movable elements by which the contents of the first and second containers can be forced through said first and second exits as the first and second movable elements are moved from first and second starting positions towards first and second ending positions;
   first and second drive stems drivingly coupled to the first and second movable elements; and
   reciprocal drive means for reciprocally driving the first and second drive stems so to drive the first and second movable elements from the first and second starting positions towards the first and second ending positions in a cyclic manner, the reciprocal drive means including:
      first and second reciprocating drivers drivingly coupled to the first and second drive stems by one-way drive elements; and
      means for adjusting the relative distances the first and second reciprocating drivers and the first and second drive stems associated therewith travel during each cycle of the reciprocal drive means so the amounts and proportions of the contents of the first and second containers forced through the first and second exits during one or more cycles of the reciprocal drive means can be selected by the user while said amounts and proportions remain the same unless said relative distances are changed.

2. The dispenser of claim 1 wherein the housing is a clear plastic housing.

3. The dispenser of claim 1 wherein the variable volume containers include cartridges configured to contain pharmaceuticals.

4. The dispenser of claim 1 wherein said adjusting means includes a rotatable dose control element for each of said first and second reciprocating drivers by which a user selects said amounts and proportions of the contents of the respective first and second containers forced through the first and second exits.

5. The dispenser of claim 4 wherein each rotatable dose control element is an axially telescoping element to permit the user to easily rotatably manipulate one said dose control element without substantial interference from another said dose control element.

6. The dispenser of claim 1 wherein the first and second drive stems have serrated outer surfaces.

7. The dispenser of claim 1 further comprising means for indicating the amounts of the contents of each of the first and second containers which are to be forced through the first and second exits during the one or more cycles of the reciprocating drive means.

8. The dispenser of claim 7 wherein the indicating means includes first and second visual displays.

9. The dispenser of claim 8 wherein the housing has first and second sides facing in opposite directions, said first and second displays located at the first and second sides, respectively.

10. The dispenser of claim 7 wherein the indicating means includes:
    first and second axially movable indicators coupled to the first and second movable elements; and
    means for magnifying the axial movement of the first and second indicators over the corresponding axial movement of the first and second movable elements.

11. A variable proportion dispenser comprising:
    a housing;
    first and second variable volume containers carried by the housing; and
    a reciprocating drive assembly comprising:
       first and second drive stems adapted to engage the first and second variable volume containers to drive the contents of the variable volume containers therefrom;
       a sliding body slidably mounted to the housing for movement in delivery and return directions;
       a first reciprocating driver, carried by the sliding body, coupled to the first drive stem, the first reciprocating driver and the first drive stem configured so that the first reciprocating driver can move the first drive stem towards the first variable volume container only if the sliding body is moving in the delivery direction;
       means for adjusting the amount the first reciprocating driver moves the first drive stem towards the first variable volume container during the movement of the sliding body in the delivery direction; and
       a one-way drive device, carried by the sliding body, configured to drive the second drive stem towards the second variable volume container when the sliding body moves in the delivery direction.

12. The dispenser of claim 11 wherein the variable volume containers are cartridges configured to contain pharmaceuticals and the housing is a clear plastic housing to provide visual access to the contents of the pharmaceutical cartridges.

13. The dispenser of claim 11 wherein the first and second drive stems have serrated outer surfaces.

14. The dispenser of claim 11 wherein the one-way drive device includes a second reciprocating driver, coupled to the second drive stem, configured so that the second reciprocating driver can move the second drive stem towards the second variable volume container only if the sliding body is moving in the delivery direction.

15. The dispenser of claim 14 wherein the one-way drive device includes means for adjusting the amount the second reciprocating driver moves the second drive stem towards the second variable volume container during the movement of the sliding body in the delivery direction.

16. A variable proportion dispenser for dispensing multiple doses of first and second flowable materials at a chosen volumetric ratio comprising:
    a housing;

first and second variable volume containers, containing the first and second flowable materials, carried by the housing;

a sliding body reciprocally mounted to the housing for movement parallel to an axis between first and second positions;

first and second drive stems operably coupled to the first and second variable volume containers, the second drive stem operably coupled to the sliding body for movement parallel to the axis;

a one-way reciprocating driver operably coupled to the first drive stem for driving the first stem towards the first variable volume container;

a dosage adjustor adjustably mounted to the sliding body to vary the axial position of the dosage adjustor relative to the sliding body;

the driver and the dosage adjustor having mating portions configured to drivingly couple the dosage adjustor to the driver when the sliding body is moved from the first position to the second position, and to permit the dosage adjustor to be decoupled from the driver when the sliding body is at an intermediate position between the first and second positions as the sliding body is moved from the second position to the first position; and the housing and the driver including stop members positioned so that when the stop members are engaged, the movement of the driver is halted when the sliding body reaches the intermediate position as the sliding body moves from the second position to the first position so to disengage the reciprocating driver from the dosage adjustor.

* * * * *